United States Patent [19]

Foltz

[11] Patent Number: 4,617,015
[45] Date of Patent: Oct. 14, 1986

[54] VISUAL PRESSURE INDICATOR FOR ENDOTRACHEAL CUFF

[75] Inventor: Carl L. Foltz, North Largo, Fla.

[73] Assignee: Halkey-Roberts Corporation, St. Petersburg, Fla.

[21] Appl. No.: 640,074

[22] Filed: Aug. 10, 1984

[51] Int. Cl.[4] .............................................. A61M 25/00
[52] U.S. Cl. ................................ 604/100; 128/207.15; 116/DIG. 9
[58] Field of Search ................................. 604/100, 99; 128/207.15; 116/DIG. 9

[56] References Cited

U.S. PATENT DOCUMENTS

| | | | |
|---|---|---|---|
| 3,656,482 | 4/1972 | Sunnen | 604/237 |
| 4,143,616 | 3/1979 | Bible | 116/266 |
| 4,361,107 | 11/1982 | Gereg | 604/100 X |
| 4,370,982 | 2/1983 | Reilly | 604/100 X |

Primary Examiner—Stephen C. Pellegrino
Attorney, Agent, or Firm—Stein, Reese & Prescott

[57] ABSTRACT

The invention comprises a visual pressure indicator for endotracheal cuffs. More particularly, the indicator of the invention comprises an indicating diaphragm which is sealingly positioned within a body by means of a cap. A hole is positioned within the cap to allow protrusion of an indicating stem of the diaphragm. The air space between the diaphragm and the body is connected in fluid communication with the cuff supply tube by means of passageways. A syringe-operable, one-way valve is positioned within the body to allow filling of the endotracheal cuff with air by means of a syringe, and to prevent leakage of the air from the cuff once it is properly filled. The indicator of the invention is fitted to the end of the cuff supply tube, and a conventional syringe is fitted to the indicator. When the endotracheal tube is in position within the patient's trachea, the syringe is operated to force air into the endotracheal cuff via the one-way valve, cuff supply tube, and cuff supply channel. The indicating diaphragm of the indicator flexes as the pressure within the cuff increases. As this pressure increases, the indicating stem of the diaphragm increasingly protrudes from the hole in the cap affixed to the body of the indicator.

5 Claims, 2 Drawing Figures

VISUAL PRESSURE INDICATOR FOR ENDOTRACHEAL CUFF

BACKGROUND OF THE INVENTION

1. Field of the Invention

This invention relates to endotracheal tubes. More particularly, this invention relates to devices for indicating the degree of inflation of the cuff of the endotracheal tube when positioned within the trachea of a patient.

2. Description of Prior Art

An endotracheal tube is used during surgical procedures and in emergency situations rather than performing a tracheostomy. Conventional endotracheal tubes consist of a piece of tubing, approximately one foot in length, which has an inflatable, balloon-like device known as a cuff at its terminal end. An air inflation cuff channel is formed within the wall of the tube and opens at its terminal end within the cuff to permit inflation of the same. A small bore cuff tube is sealingly connected to the cuff channel. A valve is fitted to the end of the cuff tube allowing a conventional syringe to inflate the cuff via the cuff tube and cuff channel.

During intubation, the patient's epiglottis is pulled back with a laryngoscope and the endotracheal tube is then inserted past the epiglottis, through the vocal chords, and then into the trachea of the patient, thereby positioning the cuff of the endotracheal tube below the vocal chords and above the bronchial tubes of the patient. While holding the endotracheal tube in position, the laryngoscope is removed. The tube is then secured in place by adhesive strapping. A bite block is placed in the patient's mouth to prevent the biting of the endotracheal tube.

The cuff is inflated by affixing a syringe to the valve at the end of the cuff tube and then operating the syringe to pump air into the cuff via the cuff tube and cuff channel. Two or three pumping operations are usually necessary in order to properly inflate the cuff and provide a proper seal between the lumen of the patient's trachea and the endotracheal cuff.

Endotracheal tubes are universally used because of the many advantages over a tracheotomy. More particularly, the use of an endotracheal tube allows the passage of anesthetic and analgetic gases into the lungs and the removal of carbon dioxide. With a properly inflated cuff, a "gas-tight" endotracheal anesthesia is assured and the collection of large amounts of carbon dioxide is avoided. In addition to administering anesthetic and analgetic gases, the endotracheal tube provides a passageway for a suction catheter to be inserted into the trachea to remove any accumulation of mucus in the lung tissue, thereby significantly reducing the possibility of infection and resulting pneumonia. Finally, the endotracheal tube prevents passage of mucus, blood, saliva, irrigants, vomitus, etc. into the trachea and the lungs during a surgical procedure.

Obviously, the foregoing advantages of using an endotracheal tube cannot be accomplished if the cuff is not properly inflated to adequately seal the space between the lumen of the trachea and the cuff of the endotracheal tube itself. Accordingly, there is a tendency to over-inflate the cuff to assure that such a proper seal has been formed between the lumen of the trachea and the cuff. Unfortunately, over- or excessive inflation of the cuff beyond the point which is necessary for a proper seal results in necrosis or damage to the lumen of the trachea.

One attempt to overcome the tendency to over-inflate the cuff has been to provide a balloon or bulb in-line with the cuff supply tube. Inflation of the endotracheal cuff causes the bulb to also inflate. The anesthetist then tactilely tests the bulb between his/her forefinger and thumb to obtain an indication of the degree of inflation of the cuff itself. Obviously, this is a subjective procedure which depends on the anesthetist's ability to feel the pressure in the bulb and correlate the same to the degree of inflation of the cuff in the patient's trachea. While this bulb device is used almost universally, its limitation are apparent, particularly when used by less experienced anesthetists.

Recently, there has been developed a caged balloon or bulb which is designed to be affixed to the end of the cuff supply tube. The caged bulb consists of a thin-walled bulb which is positioned within a rigid cage. Similar to conventional bulbs, as the endotracheal cuff is inflated, the thin-walled, caged bulb is also inflated. The openings of the cage allow the anesthetist to tactilely test the degree of the inflation of the bulb. Upon over-inflation of the cuff, the bulb protrudes from the cage via the openings. A more complete disclosure of this device can be found in U.S. Pat. No. 4,134,407, the disclosure of which is hereby incorporated by reference herein.

The caged bulb described above has not been widely used in the industry. Primarily, this is because it operates substantially identically to the conventional non-caged bulb and, therefore, suffers the same disadvantages of permitting only a subjective determination of the air pressure in the endotracheal cuff. Further, the structure of the caged bulb is difficult to manufacture on a production basis and, therefore, extremely costly.

Therefore, it is an object of this invention to provide an apparatus which overcomes the aforementioned inadequacies of the prior art devices and provides an improvement which is a significant contribution to the advancement of the endotracheal tube art.

Another object of this invention is to provide a means for objectively indicating when the cuff of an endotracheal tube has been inflated to properly seal the space between the lumen of a trachea and the wall of the cuff.

Another object of this invention is to provide an indicator for objectively indicating the degree of inflation of the cuff of an endotracheal tube to assure proper inflation of the cuff during use.

Another object of this invention is to provide an indicator for an endotracheal cuff which can be used in conjunction with conventional endotracheal tubes without requiring alteration of the tube itself.

Another object of this invention is to provide an indicator for endotracheal cuffs having a simple and reliable construction which can be manufactured in production quantities at relatively low cost.

Another object of this invention is to provide an endotracheal cuff indicator having an indicating diaphragm which visually and objectively indicates to the anesthetist the degree of inflation of the endotracheal cuff.

Another object of this invention is to provide an indicator for an endotracheal cuff which is manufactured in conjunction with a syringe-operable, one-way valve which permits a conventional syringe to be fitted thereto and pumped to inflate the endotracheal cuff via the cuff tube and cuff channel and then removed from the valve whereupon the valve closes to prevent leakage of the air from the cuff.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a visual pressure indicator for endotracheal cuffs. More particularly, the indicator of the invention comprises an indicating diaphragm which is sealingly positioned within a body by means of a cap. A hole is positioned within the cap to allow protrusion of an indicating stem of the diaphragm. The air space between the diaphragm and the body is connected in fluid communication with the cuff supply tube by means of passageways. A syringe-operable, one-way valve is positioned within the body to allow filling of the endotracheal cuff with air by means of a syringe, and to prevent leakage of the air from the cuff once it is properly filled.

During use, the indicator of the invention is fitted to the end of the cuff supply tube, and a conventional syringe is fitted to the indicator. When the endotracheal tube is in position within the patient's trachea, the syringe is operated to force air into the endotracheal cuff via the one-way valve, cuff supply tube, and cuff supply channel. The indicating diaphragm of the indicator flexes as the pressure within the cuff increases. As this pressure increases, the indicating stem of the diaphragm increasingly protrudes from the hole in the cap affixed to the body of the indicator. When the stem indicates that the cuff has been properly inflated to provide an adequate seal between it and the lumen of the trachea, the syringe is removed from the body of the indicator whereupon the one-way valve is closed to prevent any leakage of the air within the cuff to the atmosphere.

It should be appreciated that the indicator of this invention provides an objective indication of the degree of inflation of the cuff. Should any air leak from the cuff by osmosis or should any of the anesthetic or analgetic gases leak into the cuff by osmosis, the resulting decrease or increase in pressure will be visually and objectively indicated to the anesthetist. The anesthetist may then take appropriate action to increase or decrease the pressure in the cuff by refitting the syringe to the body of the indicator and pumping more air into the cuff or releasing air from the cuff. Proper inflation of the cuff is therefore assured throughout the entire surgical procedure or emergency situation. Furthermore, all of the subjectiveness associated with the prior art devices is eliminated with the indicator of this invention.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
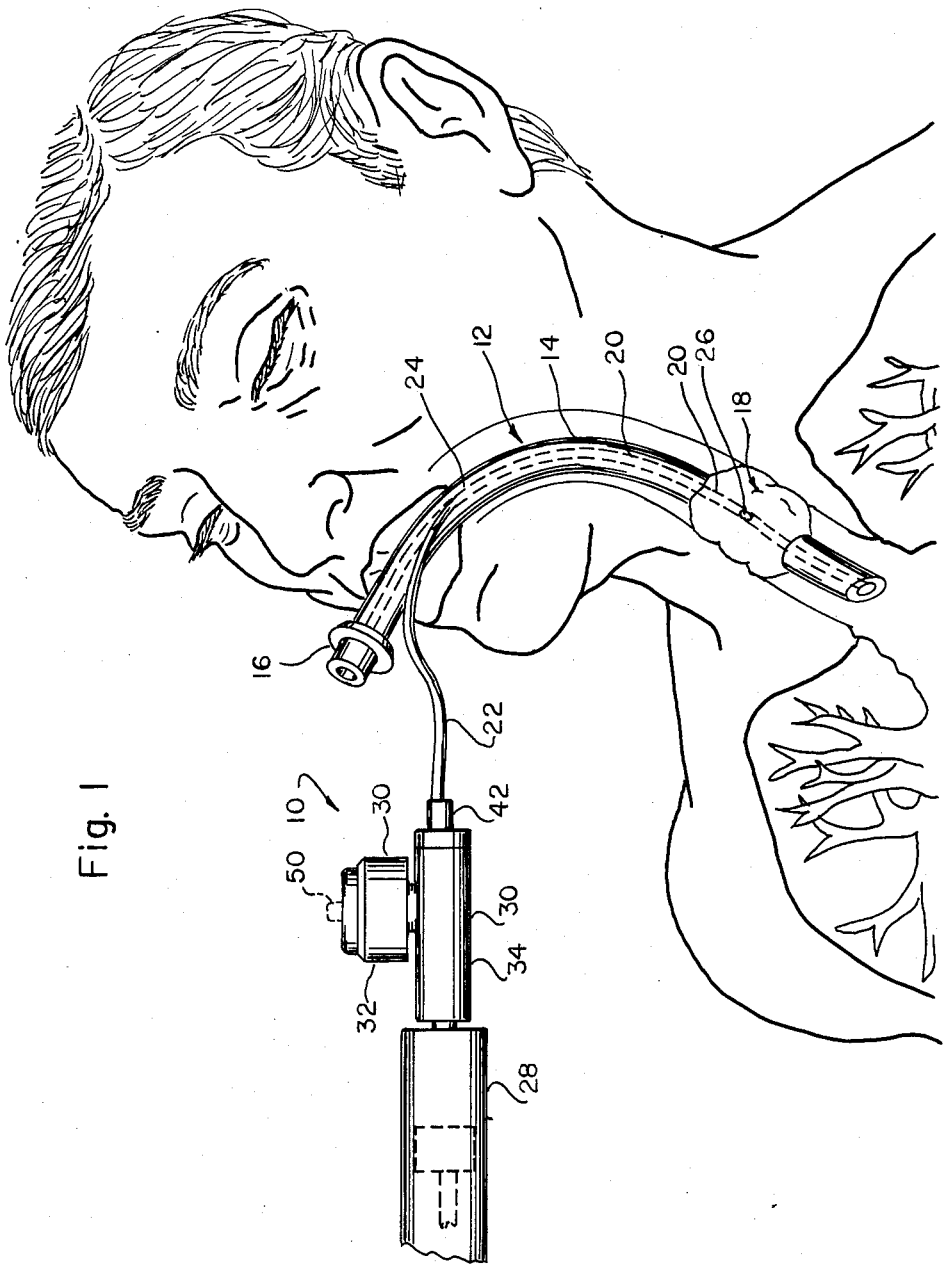
FIG. 1 is a detailed view illustrating an endotracheal tube in proper position within the trachea of a patient and having the indicator of the invention affixed to its cuff supply tube for controlling the inflation of the cuff by means of a syringe.

FIG. 1 is a detailed view illustrating the manner in which the endotracheal cuff indicator 10 of the invention is used in conjunction with conventional endotracheal tubes, generally indicated by numeral 12. Conventional endotracheal tubes 12 comprise a major tube 14 having a length of one foot or longer. A connector 16 is affixed to the proximal end of the major tube 14 to allow connection of the anesthetist's machines to the major tube 14. The endotracheal tube 12 includes an inflatable device, generally known as a cuff 18, at its terminal end. A cuff supply channel 20 is formed longitudinally within the wall of the major tube 14 along its longitudinal length. A cuff supply tube 22 is then connected in fluid communication with the cuff channel 20 at junction 24. Air forced into the cuff tube 22 flows through the cuff channel 20 into the cuff 18 itself by means of opening 26.

The endotracheal cuff indicator 10 of the invention is designed to be fitted to the end of the cuff tube 22 to allow the cuff 18 to be filled with air by means of a conventional syringe 28.

Figure 2:
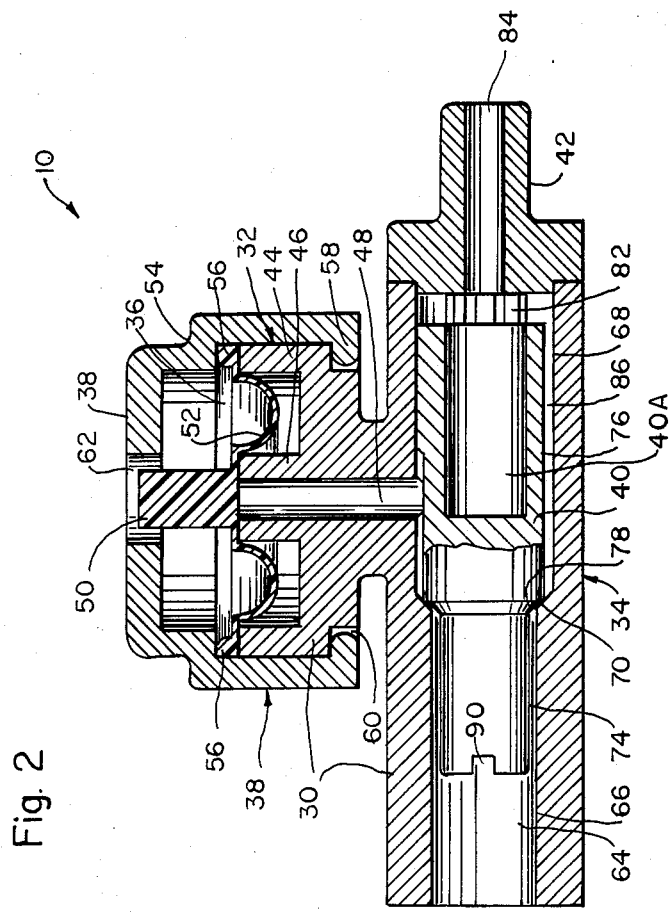
FIG. 2 is a longitudinal cross-section view of the indicator of the invention illustrating the indicating diaphragm having a stem for protruding from an opening in the cap and illustrating the syringe-operable, one-way valve.

Referring now to FIG. 2, the indicator 10 of the invention comprises a body member, generally indicated by numeral 30, having a diaphragm receiving portion 32 and a valve receiving portion 34. A diaphragm 36 is positioned in the diaphragm receiving portion 32 of the body 30, and a cap 38 is then affixed to the diaphragm receiving portion 32 to enclose the diaphragm 36 therein. A syringe-operable, reciprocating valve member 40 is positioned in the valve receiving portion 34 of the body 30, and a retainer 42 is then affixed to the valve receiving portion 34.

More specifically, the diaphragm receiving portion 32 of body 30 comprises an upstanding, annular wall 44 positioned about its periphery and a centrally located upstanding support 46. A central passageway 48 extends through the support into the valve receiving portion 34 of the body 30.

The diaphragm 36 of the indicator 10 comprises a substantially circular design having a diameter substantially equal to the diameter formed by the upper edge of the upstanding wall 44 of the body 30. The diaphragm 36 further includes a centrally located, upstanding stem 50. Preferably, stem 50 and the diaphragm 36 itself are molded integrally with one another from a resilient material such as forty durometer polyvinylchloride or silicone. Also preferably, diaphragm 36 may include an annular bellow 52 integrally formed therewith to enhance the flexing of the diaphragm 36.

The cap 38 is configured to sealingly secure the diaphragm 36 into position over the edge of the upstanding wall 44 of the body 30. Preferably, cap 38 comprises an annular step 54 whose inner edge engages the outer peripheral edge of the diaphragm 36 and forces the same against the upper edge of the upstanding wall 44. The outer peripheral edge of the diaphragm 36 may include an annular protrusion 56 to enhance the ability to seal against the upstanding wall 44 by means of the pressure exerted by the cap 38.

The cap 38 is preferably secured into position about the upstanding wall 44 of the body 30 by means of an annular protrusion 58 which extends inwardly from the cap 38 and engages into a corresponding annular notch 60 in the bottom edge of the diaphragm receiving portion 32 of the body 30.

The cap 38 further includes a centrally located opening 62 having a diameter appreciably greater than the diameter of the indicating stem 50. Preferably, the cap 38 and stem 50 are dimensioned with respect to one another in such a manner that the stem 50 does not externally protrude from opening 62 when the diaphragm 36 is in its unflexed state. Accordingly, since the stem 50 does not protrude from opening 62 during non-use, this feature assures that the stem 50 will not become damaged during shipment or storage of the indicator 10.

The valve receiving portion 34 of the body 30 of the indicator 10 includes a substantially cylindrical design having a central passageway 64 therethrough. The passageway 64 includes a reduced diameter portion 66 and an increased diameter portion 68 which together define a valve seating portion 70. The valve member 40 is designed for insertion within the passageway 64. The valve member 40 is composed of neoprene, silicone, rubber or like material and comprises a corresponding reduced diameter portion 74 and an increased diameter portion 76 which together define a corresponding valve seating portion 78. The interior 40A of the valve member 40 is hollow so that the walls of the increased diameter portion 76 are resilient.

During use, the valve member 40 is inserted into the central passageway 64 and then secured into positon by the tube adapting retainer 42. Preferably, retainer 42 is sonic welded to the wall of the valve receiving portion 34 of the body 30. When the valve member 40 is retained into position in the passageway 64, the valve seats 70 and 78 are sealingly forced together by means of a notched foot member 82 integrally formed with the retainer 42. The retainer 42 includes a central passageway 84. Fluid communication between passageways 48 and 84 is assured by means of notched channels 86 formed within the wall of the central passageway 64 of the valve receiving portion 34 and the notched foot member 82.

During use, the cuff tube 14 is sealingly fitted into passageway 84 of the retainer 42. The tip of the syringe 28 is then fitted into the other end of the indicator 10 to engage the end 88 of the valve member 40. The tip of the syringe 28 is forced inwardly to properly seal against the edge of passageway 64 while appreciably moving the valve member 40 rearwardly against the resilient force of the wall of the increased diameter portion 76, thereby breaking the seal between the valve seats 70 and 78 and opening the valve 40. The syringe 28 is then operated to force air therefrom into the cuff 18 via passageway 64, cuff tube 22 and cuff channel 20. A notch 90 may be provided in the end of the valve member 40 to assure a free flow of the air from the syringe 28.

As the pressure within the cuff 18 increases, it is apparent that the diaphragm 36 is caused to flex whereupon the indicating stem 50 begins to protrude from the cap 38 via opening 62. When the cuff 18 is properly inflated as indicated by the stem 50 extending from the cap 38, the syringe 28 is removed from the end of the body 30 whereupon valve member 40 is forced forwardly again by means of foot member 82. The valve seats 70 and 78 then sealingly engage one another.

It should be appreciated that the indicator 10 of the invention overcomes the disadvantages of the prior art devices and accomplishes the objectives set forth above. Specifically, it is apparent that the indicator 10 of the invention eliminates the subjectiveness associated with the prior art devices in indicating to the anesthetist when the cuff 18 of the endotracheal tube 12 has been properly inflated. In this regard, it is noted that the indicating stem 50 may include indicia which visually indicate the proportional amount of the indicating stem 50 extending from the cap 38 when in use.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described, what is claimed is:

1. An indicator for use in connection with an endotracheal tube having a cuff inflatable via a cuff tube, comprising in combination:
   a rigid body including a diaphragm receiving portion;
   a flexible diaphragm, said flexible diaphragm including an annular bellow integrally formed therewith to enhance the degree of movement of said stem upon flexing of said diaphragm;
   means for sealingly positioning said flexible diaphragm within said diaphragm receiving portion to define an air space, said means including a cap positioned over said diaphragm and over at least a portion of said diaphragm receiving portion, said cap including an opening aligned with said stem to permit said stem to protrude therefrom upon flexing of said diaphragm;
   means for connecting said air space in fluid communication with said cuff tube whereby said diaphragm flexes proportionally in response to pressure existing in the cuff tube and, correspondingly, in the cuff; and said diaphragm including a stem positioned to visually indicate the relative degree of pressure in the cuff tube.

2. The indicator as set forth in claim 1, wherein said diaphragm receiving portion comprises an upstanding wall on which is sealingly positioned said diaphragm by means of said cap.

3. The indicator as set forth in claim 2, wherein said diaphragm includes an annular protrusion about its periphery to enhance the sealing engagement with said upstanding wall.

4. An indicator for use in connection with an endotracheal tube having a cuff inflatable via a cuff tube, comprising in combination:

a rigid body including a diaphragm receiving portion;

a flexible diaphragm;

means for sealingly positioning said flexible diaphragm within said diaphragm receiving portion to define an air space, said means including a cap positioned over said diaphragm and over at least a portion of said diaphragm receiving portion, said cap including an opening aligned with said stem to permit said stem to protrude therefrom upon flexing of said diaphragm;

means for connecting said air space in fluid communication with said cuff tube whereby said diaphragm flexes proportionally in response to pressure existing in the cuff tube and, correspondingly, in the cuff;

said diaphragm including a stem positioned to visually indicate the relative degree of pressure in the cuff tube; and a syringe-operable, one-way valve connected in fluid communication with said cuff tube at a terminal end thereof.

5. The indicator as set forth in claim 4, wherein said syringe-operable, one-way valve comprises in combination:

said body including a valve receiving portion having a central passageway therethrough;

a valve member reciprocally mounted within said central passageway;

said central passageway and said valve member including seat engaging surfaces which seal together when said valve member is urged forwardly; and means for urging said valve member forwardly whereby, upon affixing a syringe to said valve receiving portion, said valve member is forced rearwardly to allow flowing of a fluid from the syringe through said central passageway into the cuff tube to inflate the cuff and whereby removal of the syringe from the valve receiving portion permits said valve member to move forwardly to prevent leakage of the fluid therefrom.

* * * * *